United States Patent [19]
Hogan

[11] Patent Number: 5,690,926
[45] Date of Patent: Nov. 25, 1997

[54] PLURIPOTENTIAL EMBRYONIC CELLS AND METHODS OF MAKING SAME

[75] Inventor: Brigid L. M. Hogan, Brentwood, Tenn.

[73] Assignee: Vanderbilt University, Nashville, Tenn.

[21] Appl. No.: 217,921

[22] Filed: Mar. 25, 1994

Related U.S. Application Data

[63] Continuation-in-part of Ser. No. 958,562, Oct. 8, 1992, Pat. No. 5,453,357.
[51] Int. Cl.$^6$ .................... C12N 5/06; C12N 5/16; C12N 15/09; A01N 63/00
[52] U.S. Cl. .................. 424/93.1; 424/9.1; 424/93.21; 435/172.3; 435/325; 435/352; 435/353; 435/366
[58] Field of Search .................... 800/2; 424/93.21, 424/9.1, 93.1; 435/172.3, 69.1, 240.21, 240.2; 935/40, 71

[56] References Cited

U.S. PATENT DOCUMENTS 5,166,065  11/1992  Williams et al. .................. 435/240.1

FOREIGN PATENT DOCUMENTS

WO 90/03432  4/1990  WIPO.

OTHER PUBLICATIONS

Bradley et al., 1992, "Modifying the mouse: Design and Desire", Biotechnology 10:534–539, Mar. 1992.
McMahon et al., 1990, "The Wnt-1 (int-1) proto-oncogen is required for development of a large region of the mouse brain", Cell 62:1073–1085, Sep. 21, 1990.
H.P.M. Pratt, 1987, "Isolation, culture, and manipulations of preimplantation mouse embryos", in Mammalian Development: A practical Approach, M. Monk, ed., IRL Press, Washington, DC., pp. 13–42.
Lapidot et al., Science 255:1137–1141 (1992).
Anne McLaren, Nature 359:482–483 (1992).
Reynolds & Weiss, Science, 1707–1710(1992).
Snouwaert t al., Science, 257:1083–1088 (1992).
Erwin F. Wagner, The EMBO Journal, 9:3025–3032 (1990).
Stemple and Anderson, Cell 71:973–985 (1992).
Jones et al., Nature 347:188–189 (1990).
Resnick et al., Nature 359:550–551 (1992).
Evans and Kaurman, nNture 292:154–156 (1981).
Martin, PNAS 78:7634–7638 (1981).
Bradley et al., Nature 309:255–256 (1984).
Rathjen, P.D. Genes Dev. 4:2308–2318 (1990).
Rathjen, Cell 62:1105–1114 (1990).
De Felici and McLaren, Exp. Cell Res. 144:417–427 (1983).
Wabik–Sliz and McLaren, Exp. Cell. Res. 154:530–536 (1984).
Donovan et al., Cell 44:831–838 (1986).
Dolci et al., Nature 352:809–811 (1991).
Matsui et al., Nature 353:750–752 (1991).
Stewart and Mintz, Proc. Nat'l. Acad. Sci. U.S.A. 78:6314–6318 (1981).
Mintz et al., Proc. Nat'l. Acad. Sci. U.S.A. 75:2834–2838 (1978).
Noguchi and Stevens, J. Nat'l Cancer Inst. 69:907–913 (1982).
Ginsburg et al., Development 110:521–528 (1990).
Monk et al., Development 99:371–382 (1987).
Godin et al., Nature 352:807–808 (1991).
Matsui et al., Cell 70:841–847 (1992).
Notarianni et al., Journals of Reproduction & Fertlity Supplement 41:51–56 (1990).

(List continued on next page.)

Primary Examiner—Brian R. Stanton
Attorney, Agent, or Firm—Needle & Rosenberg, P.C.

[57] ABSTRACT

The claimed invention is directed towards non-murine pluripotential cells that have the ability to be passaged in vitro for at least 20 passages and which differentiate in culture into a variety of tissues. The scope of the claimed cells includes any non-murine ES cells and particular claims are drawn to human pluripotential cells.

7 Claims, 6 Drawing Sheets

OTHER PUBLICATIONS

Smith et al., *Nature* 336:688–690 (Dec. 15, 1988).

Mummery et al., *Cell Differentiation and Development* 30:195–206 (Jun. 1, 1990).

Piedrahita et al., *Theriogenology* 29:286 (Jan. 1988).

Handyside et al., *Roux's Arch. Dev. Biol.* 196:185–190 (1987).

Flake et al., *Science* 233:776–778 (Aug. 15, 1986).

Ware et al., Biology of Reproduction Supp. 38:129 (1988).

Robertson et al. *Nature* 323:445–448 (1986).

Labosky et al., *1994 Germline development*, Wiley, Chichester (Ciba Foundation Symposium 182) pp. 1557–178.

Patent application abstract, U.S. Serial No. 07/958,009, Apr. 1, 1993.

Mar. 25, 1994 letter from Judith Plesset, Ph.D., Technology Licensing Specialist, Office of Technology Transfer, Department of Health and Human Services, National Institutes of Health, reporting abandonment of U.S. Serial No. 07/958,009.

PLURIPOTENTIAL EMBRYONIC CELLS AND METHODS OF MAKING SAME

This application is a continuation-in-part of U.S. Ser. No. 07/958,562, filed Oct. 8, 1992, now U.S. Pat. No. 5,453,357.

This invention was made with government support under grant number HD25580-04 from the National Institute of Health Child Health and Development. The United States government has certain rights in the invention.

BACKGROUND OF THE INVENTION

1. Field of the Invention

This invention relates to pluripotential embryonic stem cells and methods and compositions for making pluripotential embryonic stem cells.

2. Background Art

Primordial germ cells (PGCs) in the mouse are thought to be derived from a small population of embryonic ectoderm (epiblast) cells set aside at the egg cylinder stage prior to gastrulation (Lawson and Pederson, 1992), or even earlier (Soriano and Jaenisch, 1986). By 7 days post coitum (p.c.) about 100 alkaline phosphatase (AP) positive PGCs can be detected in the extra embryonic mesoderm just posterior to the definitive primitive streak (Ginsberg et al., 1990). These cells continue to proliferate and their number increases rapidly to around 25,000 at 13.5 days p.c. (Mintz and Russell, 1957; Tam and Snow, 1981). At the same time the PGCs migrate from the base of the allantois along the hind gut and reach the genital ridges by 11.5 days p.c. In the genital ridge, PGCs stop dividing at around 13.5 days p.c., and enter either mitotic arrest in the developing testis or meiosis in the ovary. In a few strains of mice, e.g. 129, this normal program can be disrupted if the male genital ridge from an 11.5 to 12.5 days p.c. embryo is grafted to an ectopic site such as the testis or kidney capsule. Under these conditions some PGCs give rise to teratomas and transplantable teratocarcinomas containing pluripotential embryonal carcinoma (EC) stem cells (Stevens and Makerisen, 1961; Stevens, 1983; Noguchi and Stevens, 1982).

Previous studies have shown that steel factor (SF) and leukemia inhibitory factor (LIF) synergistically promote the survival and in some eases the proliferation of mouse PGCs in culture (Godin et al., 1991; Dolci et al., 1991; Matsui et al., 1991). However, under these conditions, PGCs have a finite proliferative capacity that correlates with their cessation of division in vivo. A similar finite proliferative capacity has been reported for oligodendrocyte-type 2 astrocyte (O-2A) progenitor cells in the rat optic nerve. In this case, PDGF is involved in the self renewal growth of O-2A cells (Noble et al., 1988; Raft et al., 1988). After a determined number of cell divisions, O-2A cells may lose their responsiveness to PDGF and start differentiating into oligodendrocytes. If both PDGF and basic fibroblast growth factor (bFGF) are added in culture, O-2A progenitor cells keep growing without differentiation (Bogler et al., 1990).

Since pluripotential embryonic stem cells (ES) can give rise to virtually any mature cell type they are of great value for uses such as creating genetically manipulated animals. However, according to the published scientific literature, it has previously been possible only to obtain ES cells from mice. These murine ES cells were obtained from cultures of early blastocysts. Attempts at isolating ES cells from other animals apparently have failed. One patent publication, Evans et al., published Apr. 5, 1990 under PCT Publication WO 90/03432, claims that pluripotential ES cells can be obtained from ungulate blastocysts in vitro. The application claims that these cells are expected to be epithelial and to have a very different morphology to mouse ES cells because ungulate embryos normally form an "embryonic disc". This appears to be the basis of the allegation that the cells which they grow out of pig and cow blastocysts and which have a more epithelial morphology than mouse ES cells are, in fact, ES cells. However, mouse embryos also develop an epithelial layer of pluripotential embryonic ectoderm or epiblast cells. This layer is called an "egg cylinder" rather than an "embryonic disc". Therefore, there is apparently no strong embryological reason why the ungulate ES cells should have a different morphology to mouse ES cells. In addition, the evidence presented in the Evans application for the differentiation of the cow and pig putative ES cell lines into differentiated cell types in monolayer culture, in embryoid bodies and in tumors, is not convincing. Therefore, there is a great need to produce and maintain ES cells from a variety of different animals.

The present invention satisfies this need by demonstrating that, in the presence of bFGF, SF and LIF, PGCs continue to proliferate in culture and give rise to colonies of ES cells. These stem cells can give rise to a wide variety of mature, differentiated cell types both in vitro and when injected into nude mice and when combined with embryos to form a chimera.

SUMMARY OF THE INVENTION

The present invention provides a non-mouse, including human, pluripotential embryonic stem cell which can:

(a) be maintained on feeder layers for at least 20 passages; and (b) give rise to embryoid bodies and multiple differentiated cell phenotypes in monolayer culture.

In addition, in non-humans, the cells can form chimeras when combined with host embryos and give rise to mature sperm.

The invention further provides a method of making a pluripotential embryonic stem cell comprising culturing primordial germ cells, embryonic ectoderm cells and/or germ cell progenitors in a composition comprising a growth enhancing amount of basic fibroblast growth factor, leukemia inhibitory factor, membrane associated steel factor, and soluble steel factor to primordial germ cells under cell growth conditions, thereby making a pluripotential embryonic stem cell.

Also provided are compositions useful to produce the pluripotent embryonic stem cells and methods of screening associated with the method of making the embryonic stem cell.

BRIEF DESCRIPTION OF THE DRAWINGS

(A) PGCs from 8.5 day p.pc. embryos were seeded into wells containing SlSl[4] feeder cells either alone (open circles) or with soluble rSF (closed circles), soluble rSF and LIF (closed squares), or soluble rSF, LIF and bFGF (closed triangles). Cultures were fixed and the number of AP positive cells counted.

(B) As in (A) except that cells were cultured without added factors (open circles), with soluble rSF (closed circles), with bFGF (closed triangles) or with soluble rSF and bFGF (open triangles).

(C) As in (A) except that cells were cultured on Sl[4]-m220 cells either alone (open circles) or with soluble rSF (closed circles), soluble rSF and LIF (closed squares), soluble rSF and bFGF (open triangles) and soluble rSF, LIF and bFGF (closed triangles).

Each experiment was carried out with duplicate wells and numbers are the means+s.e.m. of three separate experiments.

(A) Primary culture after 4 days in the presence of LIF. Note that the AP positive cells are scattered among the feeder cells.

(B) Primary culture after 4 days in the presence of soluble rSF, LIF and bFGF. Note that the AP positive cells now form tight clumps.

(C) As for B, but after 6 days in culture.

(D) Secondary culture after 6 days in the presence of soluble rSF, LIF, and bFGF In this colony all the cells are AP positive.

(E) As for D except that cells at the edges of the colony are AP negative.

(F) PGCs from 12.5 day p.c. male genital ridge were cultured for 6 days in the presence of soluble rSF, LIF and bFGF. Colonies of tightly packed AP positive cells are present.

(G) Colony of ES-like cells in a secondary culture with soluble SF, LIF and bFGF stained with SSEA-1 monoclonal antibody and for AP activity. Phase contrast microscopy.

(H) The same colony as in G viewed by fluorescence microscopy. AP positive cells also express SSEA-1.

(I) Colony grown under same conditions as (G) but stained without primary antibody Scale bars=200/μm.

FIG. 3 shows the effect of growth factors on male and female PGCs in culture. Cells were dissociated from either male (squares) or female (circles) genital ridges from 12.5 day p.c. mouse embryos and cultured on $Sl^4$-m220 feeder cells either alone (empty symbols) or with soluble rSF, LIF and bFGF (filled symbols). Cells were fixed and the number of AP positive cells counted. The experiment was carried out three times, with duplicate wells.

(A) Colony of densely packed ES-like cells obtained from PGCs of an 8.5 day p.c. embryo grown on $Sl^4$-m220 cells in the presence of soluble rSF, LIF and bFGF for 6 days. Scale bar=100 μm.

(B) Simple embryoid bodies with an outer layer of endoderm (arrows) obtained after culturing PGC-derived ES cells for 4 days in suspension.

(C) Section of a teratoma obtained by injecting ES-like cells derived from PGCs of an 8.5 day p.c. embryo into a nude mouse. The region shown here contains neural tissue and pigmented epithelium. Scale bar=200 μm.

(D) Region of the same tumor as in (C) showing a dermoid cyst and secretory epithelium.

(E) Region of the same tumor as in C and D, showing bone and cartilage. The differentiated tissues shown in C-E were seen in addition to other tissue types in multiple tumors from all three lines tested.

FIGS. 5A, 5B and 5C are different magnifications of the same colony. The shadow in FIG. 5A is the edge of the well in which the cells were growing.

DETAILED DESCRIPTION OF THE INVENTION

The term "embryonic ectoderm" is used herein. "Embryonic ectoderm" and "epiblast" can be used interchangeably to refer to the same cell type.

A "pluripotential embryonic stem cell" as used herein means a cell which can give rise to many differentiated cell types in an embryo or adult, including the germ cells (sperm and eggs). Pluripotent embryonic stem cells are also capable of self-renewal. Thus, these cells not only populate the germ line and give rise to a plurality of terminally differentiated cells which comprise the adult specialized organs, but also are able to regenerate themselves. This cell type is also referred to as an "ES cell" herein.

A "fibroblast growth factor" (FGF) as used herein means any suitable FGF. There are presently seven known FGFs (Yamaguchi et al. (1992)). These FGFs include FGF-1 (acidic fibroblast growth factor), FGF-2 (basic fibroblast growth factor), FGF-3 (int-2), FGF-4 (hst/K-FGF), FGF-5, FGF-6, FGF-7 and FGF-8. Each of the suitable factors can be utilized directly in the methods taught herein to produce or maintain ES cells. Each FGF can be screened in the methods described herein to determine if the FGF is suitable to enhance the growth of or allow continued proliferation of ES cells or their progenitors. Various examples of FGF and methods of producing an FGF are well known; see, for example, U.S. Pat. Nos. 4,994,559; 4,956,455; 4,785,079; 4,444,760; 5,026,839; 5,136,025; 5,126,323; and 5,155,214.

"Steel factor" (SF) is used herein. SF is also called stem cell factor, mast cell growth factor and c-kit ligand in the art. SF is a transmembrane protein with a cytoplasmic domain and an extracellular domain. Soluble SF refers to a fragment cleaved from the extracellular domain at a specific proteolytic cleavage site. Membrane associated SF refers to both normal SF before it has been cleaved or the SF which has been altered so that proteolytic cleavage cannot take place. SF is well known in the art; see European Patent Publication No. 0 423 980 A1, corresponding to European Application No. 90310889.1.

"Leukemia Inhibitory Factor" (LIF) is also used herein. LIF is also known as DIA or differentiation inhibiting activity. LIF and uses of LIF are also well known; see for example U.S. Pat. Nos. 5,187,077 and 5,166,065.

It should be recognized that FGF, SF and LIF are all proteins and as such certain modifications can be made to the proteins which are silent and do not remove the activity of the proteins as described herein. Such modifications include additions, substitutions and deletions. Methods modifying proteins are well established in the art (Sambrook et al., *Molecular Cloning: A Laboratory Manual*, 2nd Ed., Cold Spring Harbor Laboratory, Cold Spring Harbor, N.Y., 1989).

This invention provides a non-mouse pluripotential ES cell which can be maintained on feeder layers for at least 20 passages, and give rise to embryoid bodies and multiple differentiated cell phenotypes in monolayer culture. Only those non-mouse animals which can be induced to form ES cells by the described methods are within the scope of the invention. Given the methods described herein, an ES cell can be made for any animal. However, mammals are preferred since many beneficial uses of mammalian ES cells exist. Mammalian ES cells such as those from rats, rabbits, guinea pigs, goats, pigs, cows, and humans can be obtained. Alternatively, embryos from these animals can be screened for the ability to produce ES cells.

The ES cells of this invention can be maintained for at least 20 passages. However, the ES cells can be capable of indefinite maintenance. Typically, after about 10 passages the cells are frozen so that the starting population is not altered by minor chromosomal alterations.

Once the non-mouse ES cells are established, they can be genetically manipulated to produce a desired characteristic. For example, the ES cells can be mutated to render a gene non-functional, e.g. the gene associated with cystic fibrosis or an oncogene. Alternatively, functional genes can be inserted to allow for the production of that gene product in an animal, e.g. growth hormones or valuable proteins. Such methods are very well established in the art (Sedivy and Joyner (1992)).

The invention also provides a composition comprising:

(a) pluripotential ES cells; and (b) an FGF, LIF, membrane associated SF, and soluble SF in amounts to enhance the growth of and allow the continued proliferation of the cell. Thus, this composition represents the composition after primordial germ cells, embryonic ectoderm or germ cells have become pluripotential ES cells. The pluripotential ES cells can continue to be maintained in this composition or alternatively they can be maintained on a feeder layer. Optimally, HF can be added to the feeder layer.

Also provided is a composition comprising an FGF, LIF, membrane associated SF, and soluble SF in amounts to enhance the growth of, and allow the continued proliferation of primordial germ cells and the formation of pluripotent ES cells from the primordial germ cell. This composition need not include primordial germ cells but comprises the various growth factors in amounts that promote the growth, proliferation and formation of pluripotent ES cells. Thus, this composition can be sufficient for the establishment of pluripotent ES cells from embryonic ectoderm cells or germ cells.

Also provided is a composition comprising: (a) mammalian primordial germ cells and/or germ cells and/or embryonic ectoderm cells; and (b) a fibroblast growth factor, leukemia inhibitory factor, membrane associated steel factor and soluble steel factor in amounts to enhance the growth and allow the continued proliferation of the cells and the formation of pluripotent embryonic stem cells.

Typically, the compositions of the invention include a feeder layer. Feeder layers can either be cells or cell lines cultured for the purpose of culturing pluripotent ES cells. Alternatively, feeder layers can be derived from or provided by the organ or tissue in which the primordial germ cells, embryonic ectoderm cells or germ cells are located, e.g. the gonad. Thus, if the somatic cells of the tissue or organ in which the desired cells are located are sufficient to provide the appropriate culture environment, a separate feeder layer is not required. Alternatively, the feeder cells could be substituted with extracellular matrix plus bound growth factors. Feeder layers which are representative of those which can be utilized are set forth in the Examples. Naturally, the membrane associated SF can be contained on the cells of such a feeder layer.

The compositions arise from the fact that FGF, LIF and SF are used either to enhance the growth and proliferation of primordial germ cells and/or embryonic ectoderm cells to become ES cells. Growth and proliferation enhancing amounts can vary depending on the species or strain of the cells, and type or purity of the factors. Generally, 0.5 to 500 ng/ml of each factor within the culture solution is adequate. In a more narrow range, the amount is between 10 to 20 ng/ml for bFGF and LIF and between 10 to 100 ng/ml for SF. Regardless of whether the actual amounts are known, the optimal concentration of each factor can be routinely determined by one skilled in the art. Such determination is performed by titrating the factors individually and in combination until optimal growth is obtained. Additionally, other factors can also be tested to determine their ability to enhance the effect of FGF, LIF and SF on ES cell proliferation. As described below, such other factors, or combinations of factors when used to enhance ES cell proliferation can be included within the above compositions. Also, compounds and fragments of FGF, LIF and SF which mimic the function of these factors can be used to enhance the growth and proliferation of the cells to become ES cells and are included within the scope of the invention.

The factors are essential to the formation of pluripotent ES cells. Thus, the amount of the factors utilized is determined by the end result of the pluripotent ES cells. However, the factors also serve to enhance the growth and allow the continued proliferation of the cells. Relatedly, the factors also appear to help the cells survive.

Alternatively, FGF, LIF, and SF can be used to maintain ES cells. The amounts of FGF, LIF and SF necessary to maintain ES cells can be much less than that required to enhance growth or proliferation to become ES cells. However, the cells may be maintained on a feeder layer without the addition of growth factors. Optimally, LIF can be added to enhance maintenance.

In general, FGF or LIF from a species different from the source of the ES, primordial germ cell, germ cell or embryonic ectoderm cell can be utilized. However, all the factors utilized and especially the SF utilized are preferably from the same species as the utilized cell type. However, FGF, LIF or SF from various species can be routinely screened and selected for efficacy with a cell from a different species. Recombinant fragments of FGF, LIF or SF can also be screened for efficacy as well as organic compounds derived from, for example, chemical libraries.

The invention also provides a method of making a pluripotential ES cell comprising administering a growth enhancing amount of FGF, LIF, membrane associated SF, and soluble SF to primordial germ cells and/or embryonic ectoderm cells under cell growth conditions, thereby making a pluripotential ES cell. Thus, primordial germ cells and embryonic ectoderm cells can be cultured as a composition in the presence of these factors to produce pluripotent ES cells. As noted above, typically the composition includes a feeder layer.

The invention also provides a method of making a mammalian pluripotential embryonic stem cell comprising culturing a germ cell or a composition from postnatal mammalian testis in a composition comprising a growth enhancing amount of basic fibroblast growth factor, leukemia inhibitory factor, membrane associated steel factor, and soluble steel factor, thereby making a pluripotential embryonic stem cell from a germ cell. "Germ cells" as used herein means the cells which exist in neonatal or postnatal testis and are the progenitors of gametes. In the testis, these germ cells represent a small population of stem cells capable of both self-renewal and differentiation into mature spermatogonia. Thus, "germ cells" are the postnatal equivalent to the prenatal primordial germ cells and can include primitive or immature spermatogonia such as type A spermatogonia or any undifferentiated early stage cell that can form a pluripotent embryonic stem cell.

These methods can be practiced utilizing any animal cell, especially mammal cells including mice, rats, rabbits, guinea pigs, goats, cows, pigs, humans, etc. The ES cell produced by this method is also contemplated.

Also provided is a method of screening cells which can be promoted to become an ES cell comprising contacting the cells with FGF, LIF, membrane associated SF, and soluble SF in amounts to enhance the growth of and allow proliferation of the cells and determining which cells become ES cells. Utilizing this method, cells other than primordial germ cells, germ cells, and embryonic ectoderm cells can be selected as a source of ES cells.

Since the invention provides ES cells generated from virtually any animal, the invention provides a method of using the ES cells to contribute to chimeras in vivo in non-humans comprising injecting the cell into a blastocyst and growing the blastocyst in a foster mother. Alternatively, aggregating the cell with a non-human morula stage embryo and growing the embryo in a foster mother can be used to produce a chimera. Chimeric animals can subsequently be bred to obtain germ line transmission of ES cell traits. As discussed above, the ES cells can be manipulated to produce a desired effect in the chimeric animal. The methods of producing such chimeric animals are well established (Robertson (1987)).

Alternatively, the ES cells can be used to derive cells for therapy to treat an abnormal condition. For example, derivatives of human ES cells could be placed in the brain to treat a neurodegenerative disease. Relatedly, ES cells can be used to screen factors to determine which factors produce derivative (more differentiated) cells. Many standard means to determine the presence of a more differentiated cell are well known in the art.

FGF, SF and LIF have been shown herein to be critical for making ES cells. However, as noted above for FGF, other members of the respective growth factor family could also be used to make ES cells. Thus, later discovered members of each family can merely be substituted to determine if the new factor enhances the growth and allows the continued proliferation of PGCs or embryonic ectoderm cells to form ES cells. For example, if a new member of the LIF family is discovered, the new LIF is merely combined with SF and FGF to determine if the new family member enhances the growth and allows the continued proliferation of PGCs or embryonic ectoderm cells. Thus, this invention provides the use of family members and a method of screening family members for activity.

Likewise, additional growth factors may be found useful in enhancing the growth and proliferation of PGCs or embryonic ectoderm cells from various animals. This invention provides combining FGF, SF and LIF with other growth factors to obtain or enhance the production of ES cells. Thus, a method of screening other growth factors for the ability to promote PGCs and embryonic ectoderm cells to form ES cells is also provided. In this regard, IL-11, IL-6, CNTF, NGF, IGFII, flt3/flk-2 ligand and members of the Bone Morphogenetic Protein family are good screening candidates and can be used to promote ES cell formation.

EXAMPLES

All the cell types and other materials listed below can be obtained through available sources and/or through routine methods.

MATERIALS AND METHODS

Feeder cells

The Sl/Sl$^4$ cell line, derived from a homozygous null Sl/Sl mouse embryo, and its derivative, Sl$^4$-m220, which stably expresses only membrane bound murine SF lacking exon 6 encoding the proteolytic cleavage site, were obtained from Dr. David Williams (Howard Hughes Medical Institute, Indiana University Medical School). Other cell lines which produce adequate SF can be substituted for SlSl$^4$, for example mouse or human embryo fibroblasts or cell lines or somatic cell lines from gonads or genital ridges. Combinations of feeder cells can also be utilized. They were maintained in DMEM with 10% calf serum and 50 ug/ml gentamicin. For making feeder layers they were irradiated (500 rads) and plated at a density of 2×105 per well of 24-well plates (Falcon) in the same medium, 24 hrs before use. Wells were pre-treated with 1% gelatin. STO cells stably transfected with human LIF and the bacterial neor gene (SLN) were obtained from Dr. Allan Bradley.

Primary cultures of PGCs

Embryos were from ICR females mated with (C57BLxDBA)F1 males. Noon of the day of plug is 0.5 day post coitum (p.c.). The caudal region of 8.5 day p.c. embryos (between the last somite and the base of the allantois) was dissociated into single cells by incubation at 37° C. with 0.05% trypsin, 0.02% EDTA in Ca$^{++}$/Mg$^{++}$ free Dulbecco's phosphate-buffered saline (PBS) for about 10 mins with gentle pipetting. At this stage there are between about 149 and 379 PGCs in each embryo (Mintz and Russell, 1957). Cells from the equivalent of 0.5 embryo were seeded into a well containing feeder cells as above and 1 ml of DMEM, 2 mM glutamine, 1 mM sodium pyrovale, 100 i.u./ml penicillin and 100 ug/ml streptomycin and 15% fetal bovine serum (PGC culture medium). Finely minced fragments of genital ridges from 1.5 and 12.5 day p.e. embryos were trypsinized as above and plated at a concentration of 0.1 embryo per well. Growth factors were added at the time of seeding, usually at the following concentrations, which were shown to be optimal for PGC proliferation; recombinant human LIF and bFGF (10–20 ng/ml) and soluble rat SF (60 ng/ml). The medium was changed every day.

Secondary culture of PGC

Primary cultures were trypsinized and reseeded into wells containing Sl$^4$-m220 feeder layers in PGC culture medium. For further subculture, rounded colonies of densely packed ES-like cells were carefully picked up in a finely drawn pipette and trypsinized in a microdrop under mineral oil before seeding into wells containing feeder cells as above. After several subcultures in this way, cultures were passaged without picking individual colonies.

Alkaline phosphatase (AP) staining

This was carried out as described (Matsui et al. 1991). After staining, AP positive cells were counted using an inverted microscope.

SSEA-1 staining

PGC cultures on Sl$^4$-m220 feeder cells on a chamber slide (Nunc) were washed twice with PBS containing 2% calf serum, 0.1% sodium azide and then incubated with mouse monoclonal antibody SSEA-1 (1:100 dilution) on ice for 30 min. After washing with PBS, cells were incubated for 30 mins with FITC-conjugated Fab' fragment of goat anti mouse IgG (H+L) (Cappell, 1:5 dilution). After washing in PBS, cells were fixed in 4% paraformaldehyde before staining for AP.

Tumors in nude mice

Approximately $2\times10^6$ cells from three independent lines were injected subcutaneously into nude mice (three mice per line). After three weeks tumors were fixed in Bouin's fixative, processed for histology and sections stained with haematoxylin and eosin.

Chimera formation

Ten to fifteen cells from two independent lines derived from 8.5 day p.c. embryos were injected into the blastocoel of 3.5 day p.c. blastocysts of either ICR or C57BL/6 mice. These were returned to the uteri of 2.5 day p.c. pseudopregnant foster mothers.

Culture of murine PGCs in the presence of growth factors

Figure 1A:
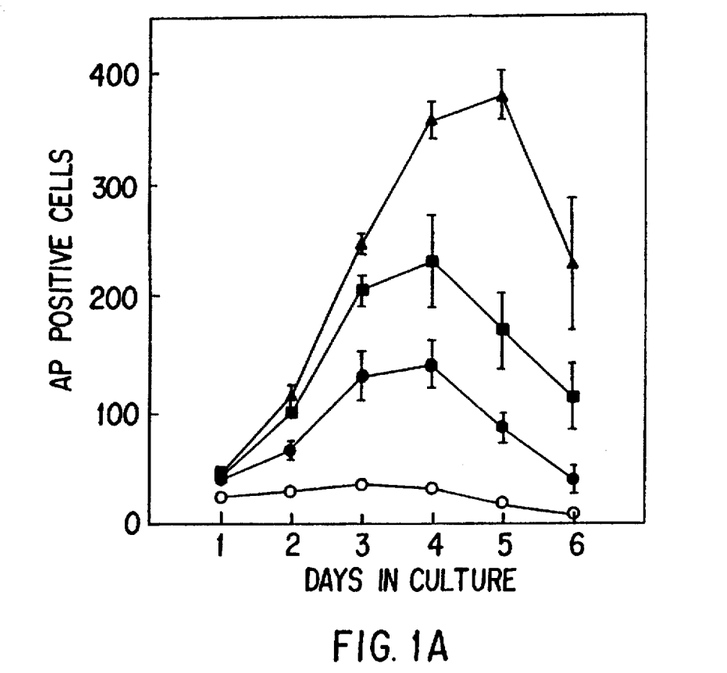
FIGS. 1A–C show the effect of growth factors on murine PGCs in culture.
Figure 1B:
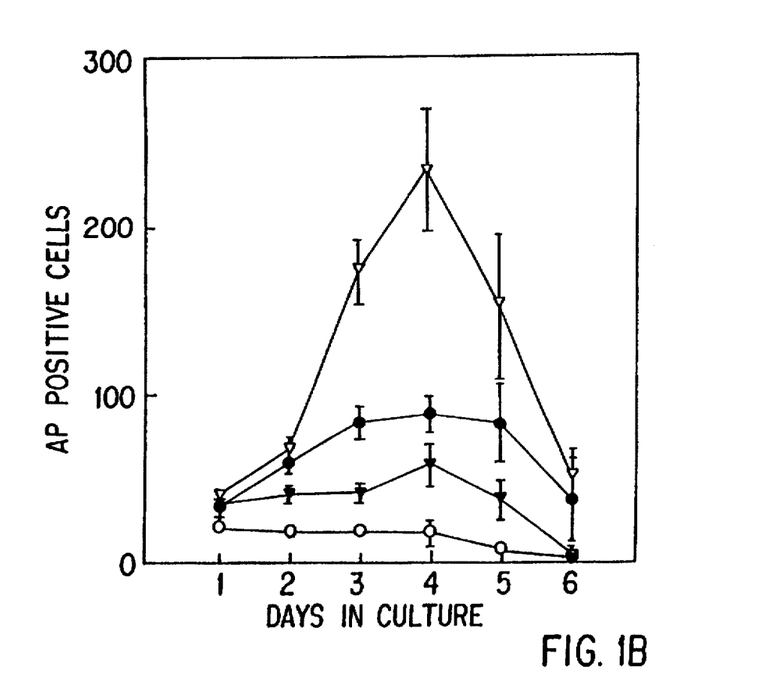

Initial experiments used $Sl/Sl^4$ cells derived from a homozygous null Sl/Sl mutant mouse as a feeder layer for the culture of cells dissociated from the posterior of 8.5 days p.c. embryos, and AP staining as a marker for PGCs (FIG. 1A). As shown previously (Matsui et al., 1991), soluble SF and LIF act synergistically on PGCs. Addition of bFGF further enhances growth, and the cells continue to increase in number until day 5 in culture, i.e. one day longer than usual. The effect of bFGF alone is small, and both SF and LIF are needed in addition to bFGF for maximal effect on PGC growth (FIG. 1A, B). A variety of other growth factors, including human activin, Bone Morphogenetic Protein-4, βNGF, and PDGF at 10 and 50 ng/ml had no effect in the presence of SF and LIF.

Figure 1C:
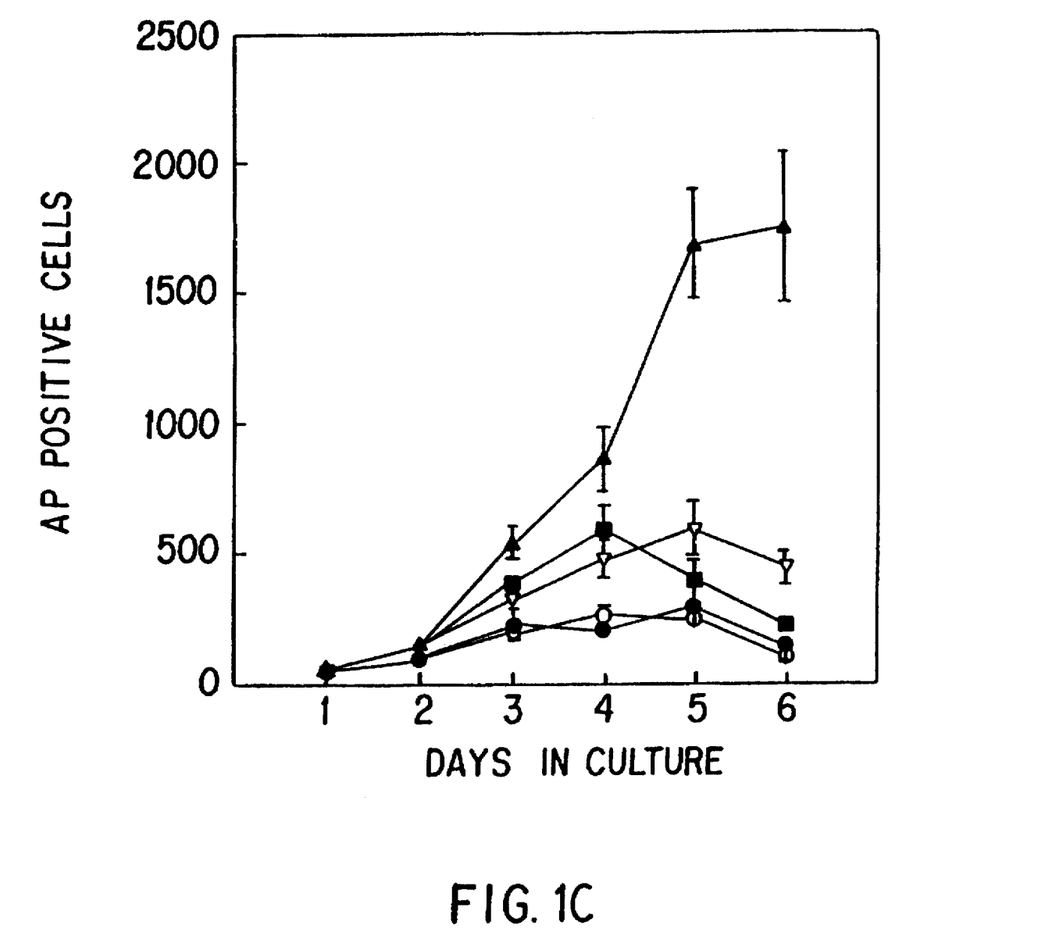

Membrane associated SF seems to play an important role in PGC proliferation since $Sl^d$ mouse mutants which make only soluble SF have a reduced number of PGCs in vivo, and membrane associated SF is more effective than soluble SF in supporting PGC growth and survival in culture (Dolci et al., 1991; Matsui et al., 1991). To test the effect of added factors in the presence of membrane associated SF, 8.5 day p.c. PGCs were cultured on $Sl^4$-m220 feeder cells, which express only membrane associated SF (Matsui et al., 1991; Toksoz et al., 1991). Both LIF and bFGF separately enhance PGC growth on $Sl^4$-m220 feeder cells with added soluble rSF. However, when LIF and bFGF are added together, PGC growth is dramatically stimulated and the cells continue to proliferate through to day 6 in culture (FIG. 1C). The cells survive until day 8, at which time the feeder layer deteriorates, but they can be trypsinized and subcultured (see below).

Figure 2A:
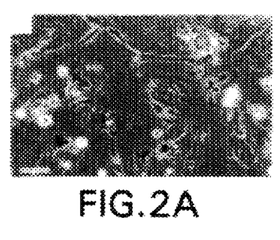
FIGS. 2A–I show the morphology of primary and secondary cultures of PGCs and their descendants. PGCs from 8.5 d p.c. embryos (A–E, G,H) or 12.5 d p.c. male genital ridges (F) were cultured on $Sl^4$-m220 cells as described and stained for AP activity.
Figure 2B:
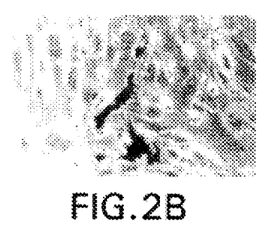
Figure 2C:
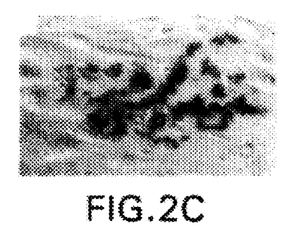
Figure 2D:
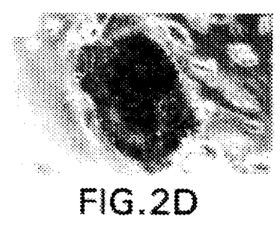

Pregonadal PGCs are motile in vivo, and when cultured with LIF on a $Sl^4$-m220 feeder layer they form burst colonies of cells with a flattened and polarized morphology, characteristic of motile cells (FIG. 2A). In contrast, PGCs cultured on a $Sl^4$-m220 feeder layer with soluble SF and bFGF or with bFGF and LIF (FIG. 2B, C), form discrete colonies of tightly packed cells. These colonies increase in size over day 6 in culture only when both bFGF and LIF are present (FIG. 2C).

Figure 2E:
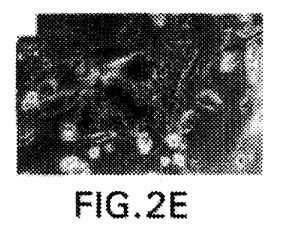

To determine whether PGCs and their descendants continue to proliferate in culture, primary colonies of PGCs were trypsinized after 6 days in culture and replated on a fresh $Sl^4$-m220 feeder layer with added growth factors. By day 6 in secondary culture, large colonies of densely packed AP positive cells resembling embryonic stem (ES) cells are present (FIG. 2D,E; FIG. 4, A), with an overall plating efficiency of about 5%. These colonies are also positive for the expression of the antigen SSEA-1, a characteristic of PGCs (Donovan et al., 1986) and undifferentiated embryonal carcinoma and ES cells (Solter and Knowles, 1978) (FIG. 2 G, H). Although the growth of primary cultures is strictly dependent on the presence of LIF and bFGF, secondary colonies can form in the absence of these factors (Table 1), indicating a reduced exogenous growth factor requirement for the descendants of PGCs after subculture. Most of the colonies show strong, uniform AP staining. However, some colonies contain only a small number of strongly stained cells, surrounded by cells which are weakly stained or negative (FIG. 2E). In many cases these negative cells are larger and have a more flattened morphology than the AP positive cells. For further subculture, individual colonies of cells with a distinctive, tightly packed, ES cell-like morphology were picked up in a micropipet, trypsinized and replated on a fresh feeder layer with added factors. Such colonies can be subcultured at least ten times and continue to give rise to colonies of similar morphology. In later passages, these cultures were transferred to feeder layers of STO cells in medium without added factors normally used for blastocyst-derived ES cell culture (Robertson, 1987). Under these conditions they continue to proliferate in an undifferentiated state, for a total of at least 20 passages.

Two independent lines at passage 14 (1/14, 2/14) and one at passage 20 (3/20) were karyotyped. Most cells had a normal or near normal XY karyotype, but in two lines (2/14 and 3/20) there was a significant proportion of trisomic cells.

Long term culture of PGC-derived cells from genital ridges

Figure 2F:
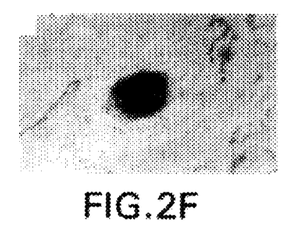
Figure 2G:
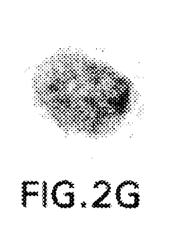
Figure 2H:
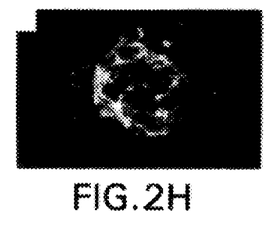
Figure 2I:
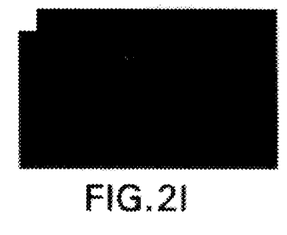
Figure 3:
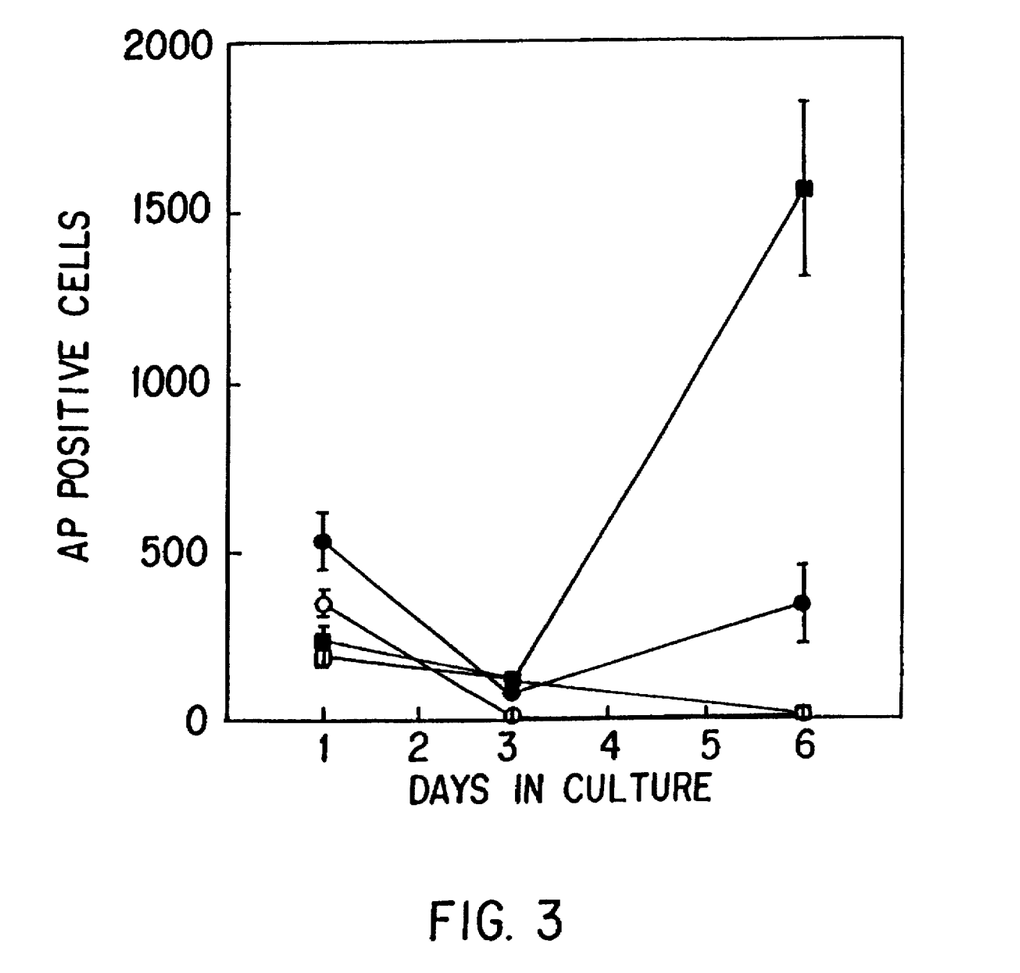

Since transplantable teratocarcinomas can be induced experimentally by grafting genital ridges from 11.5 or 12.5; days p.c. male embryos of the 129 strain to an ectopic site, we tested the possibility that ES-like cells can be obtained from genital ridges in culture. Genital ridges were trypsinized and the cells plated on an $Sl^4$-m220 feeder layer with soluble SF, LIF and bFGF. The number of PGCs initially declines but increases after 3 days, and by 6 days colonies of densely packed, AP positive cells can be seen (FIG. 2F). If cells from male and female 12.5 days p.c. genital ridges are cultured separately, male PGCs increase in number and form colonies. In contrast, only a few female PGCs form colonies (FIG. 3). The differentiation capacity of genital ridge-derived colonies has not so far been tested.

Differentiation of PGC-derived ES cells in vitro and in nude mice

Figure 4A:
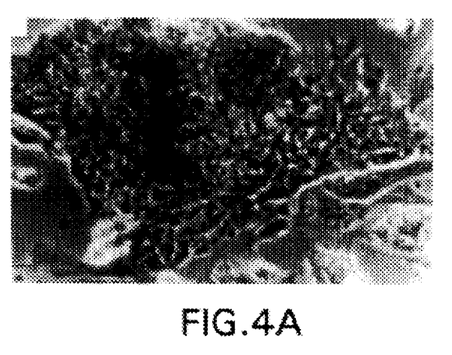
FIGS. 4A–E shows the morphology of undifferentiated PGC derived ES cells and their differentiated derivatives.
Figure 4B:
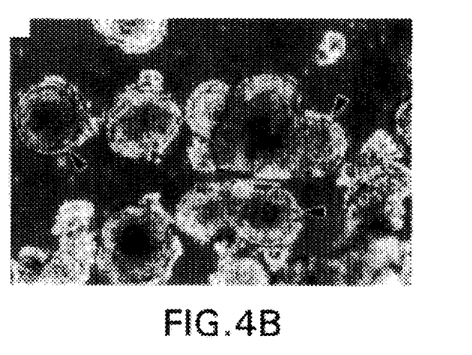

Four independent lines of undifferentiated cells derived from 8.5 day embryos and cultured onto STO feeder layers were trypsinized and pipetted gently to generate small clumps of cells which were then placed in bacteriological plastic dishes. After five to seven days most of the clumps differentiated into typical simple or cystic embryoid bodies (EBs), with a clear outer layer of extraembryonic endoderm cells (FIG. 4, B). When these EBs were returned to tissue culture plastic dishes they rapidly attached and over two weeks gave rise to a variety of cell types, including extraembryonic endoderm, spontaneously contracting muscle, nerve and endothelial and fibroblast-like cells.

Figure 4C:
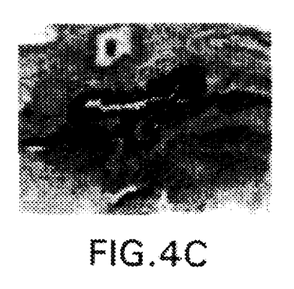
Figure 4D:
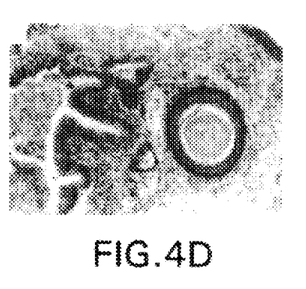
Figure 4E:
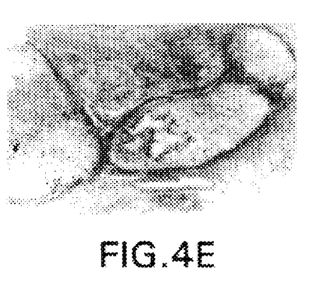

Three of these four lines, at passages 9 and 15 on STO cells, were injected subcutaneously into nude mice. Each line gave rise to multiple, well-differentiated teratocarcinomas, containing a wide variety of tissues, including keratinized, secretory and ciliated epithelium, neuroepithelium and pigmented epithelium, cartilage, bone, and muscle, as well as nests of undifferentiated embryonic cells (FIG. 4, C–E).

PGC-derived ES cells can contribute to chimeras in vivo

To test whether the descendants of PGCs in culture are able to contribute to chimeras in vivo, 10–15 cells with an ES-like morphology from two independent early passage cultures derived from 8.5 day embryos and cultured on either Sl$^4$m220 cells or STO cells were injected into host ICR or C57BL/6 blastocysts. From a total of 21 pups born, four were chimeric, as judged by coat color, but only two were extensive, with approximately 50 and 90% chimerism. The 50% coat color chimera, generated by injecting cells from the 4th passage on STO cells into an ICR blastocyst, died at 11 days after birth and showed stunted growth and skeletal abnormalities. The 90% coat color chimera, obtained by injecting cells from the 6th passage on STO cells into a C57BL/6 blastocyst, had no obvious abnormalities.

Germ line transmission
  Materials and methods
  PGC culture

Cultures are initiated as described above by dissecting C57BL/6 8.5 days p.c. embryos free of extraembryonic tissues. Fragments comprising the posterior third of the embryo (from the base of the allantois to the first somite) are then pooled, rinsed with Dulbecco's Ca$^{++}$.Mg$^{++}$ free phosphate buffered saline (PBS) and dissociated with 0.25% trypsin, 1 mM EDTA (GIBCO) and gentle pipetting. This single cell suspension is then plated in 0.1% gelatin coated 24 well dishes (Corning) with irradiated Sl/Sl$^4$ m220 cells as feeder layers at a concentration of approximately 0.5 embryo equivalents per well. The cultures were grown in Dulbecco's modified Eagle's medium (DMEM) (Specialty Media, Lavallette, N.J.) supplemented with 0.01 mM non-essential amino acids (GIBCO), 2 mM glutamine (GIBCO), 50 µg/ml gentamycin (Sigma), 15% fetal bovine serum (selected batches, Hyclone) and 0.1 mM 2-mercaptoethanol (Sigma). For these primary cultures, the medium is additionally supplemented with soluble recombinant rat SF at 60 ng/ml, bFGF at 20 ng/ml (GIBCO), and LIF at 20 ng/ml. After 6 days some of the cultures are stained for alkaline phosphatase (AP) as described above in order to assess the survival and proliferation of PGCs. After 10 days, parallel cultures are dissociated into single cells and plated onto mouse embryo fibroblast (reef) feeder layers with LIF (ESGRO, GIBCO 1000 U/ml). These cultures are monitored for the appearance of colonies of EG cells. Individual EG colonies are isolated with a micropipette and lines established. EG cultures are then maintained in the same manner as ES cell lines with irradiated mefs as feeder cells and LIF (Smith et al., 1988 and Williams et al., 1988).

Blastocyst injection

Ten to twenty EG cells at passage numbers 6 to 10 were injected into 3.5 days p.c. blastocysts from BALFl/c mice. Foster mothers were (C57BL/6×DBA)$_{F1}$ females mated to vasectomized Swiss Webster males. Injected blastocysts were transferred to the uterus of 2.5 days p.c. foster mothers (Hogan et al., 1986) and chimeric pups were identified by their coat color. Chimeras were bred to either BALB/c or ICR mice and germ line transmission was judged on the day of birth by the presence of eye pigment.

Results

Two ES lines derived from 8.5 day C57BL/6 embryos produced chimeras which transmitted the C57BL/6 genome through mature sperm (germ line transmission). This was judged by mating male chimeras with albino females and observing the production of pigmented pups. With the ES cell line known as TGC$^{85}$10, nine chimeric males were obtained and four produced pigmented pups. With the ES cell line known as TGC$^{85}$19 six chimeric males were obtained and one of these produced pigmented pups.

Generation of ES cells from other mammals

ES cells from other mammals can be produced using the methods described above for murine. The mammalian cell of choice is simply substituted for murine and the murine methods are duplicated. The appropriate species specific growth factors (e.g. SF) can be substituted for murine growth factors as necessary. Any additional growth factors which can promote the formation of ES cells can be determined by adding the growth factors to FGF, LIF, and SF as described above and monitored for an affect on ES formation.

Method for the isolation of pluripotential stem cells from human primordial germ cells and human embryonic (fetal) gonads The above methods for isolation of ES cells from murine embryos were repeated for isolation of ES cells from human embryos. Specifically, testes were dissected from a 10.5 week human embryo. Younger or older embryos represent alternative sources. The preferred age range is between 8.5 weeks and 22 weeks. Tissue was rinsed in buffered saline, and incubated in trypsin solution (0.25% trypsin, 1 mM EDTA in Ca$^{30}$ $^+$/Mg$^{++}$ free HEPES buffered saline) for 10 minutes at 37° C. The tissue was dissociated by pipetting and the cells plated into wells of a 24 well tray containing irradiated feeder cells. In this experiment the feeder cells were Sl/Sl mouse fibroblasts transfected with human membrane associated Stem Cell Factor (Sl$^4$h220 cells from Dr. David Williams, HHMI, Indiana State University School of Medicine). An alternative feeder layer would consist of a mixture of mouse or human embryo fibroblasts and Sl$^{4h220}$ cells, to provide a more coherent layer for long term cell attachment. The culture medium consists of Dulbecco's modified Eagle's medium (DMEM) with 10% fetal bovine serum supplemented with 10 ng/ml human bFGF, 60 ng/ml human Stem Cell Factor and 10 ng/ml human LIF. Alternatively, the amounts of bFGF can be increased (e.g. 20 ng/ml). Other alternative or additional supplements can be added at this time, for example IF-6, IL-11, CNTF, NGF, IGFII, flt3/flk2 ligand, and/or members of the Bone Morphogenetic Protein family. The cultures were maintained for 5 days, with daily addition of fresh growth factors. Longer culture could also be utilized, e.g. 5 to 20 days.

After 5 days, cultures were dissociated with trypsin solution as before and seeded into wells containing a feeder layer of irradiated mouse embryo fibroblasts. The medium was supplemented with growth factors daily as above. The addition of growth factors to the culture medium at this stage can be utilized, and a feeder layer of a mixture of mouse of human fibroblast and Sl$^4$h220 cells can be substituted.

Figure 5A:
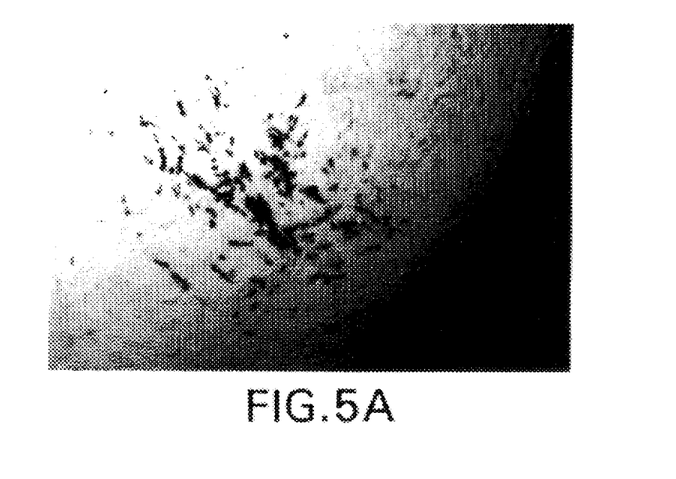
FIGS. 5A–C shows a photomicrograph of a colony of alkaline phosphatase positive cells derived in culture from an approximately 10.5 week old human embryonic testis. Following dissociation, testis cells were seeded into wells of a 24-well plate containing irradiated feeder cells ($Sl^4$ h220) and growth factors 10 ng/ml bFGF, 60 ng/ml soluble SCF and 10 ng/ml LIF). After 5 days the cells were subcultured at a dilution of 1:4 into wells containing a feeder layer of irradiated mouse embryo fibroblasts with the same cocktail of growth factors. After 10 days the cultures were fixed and stained for alkaline phosphatase activity. The colony shown here (one of many) closely resembles colonies of alkaline phosphatase positive cells derived from primordial germ cells of the mouse embryo (see FIG. 2C). In particular, the human cells associate into tightly packed clusters (see arrow in FIG. 5C).
Figure 5B:
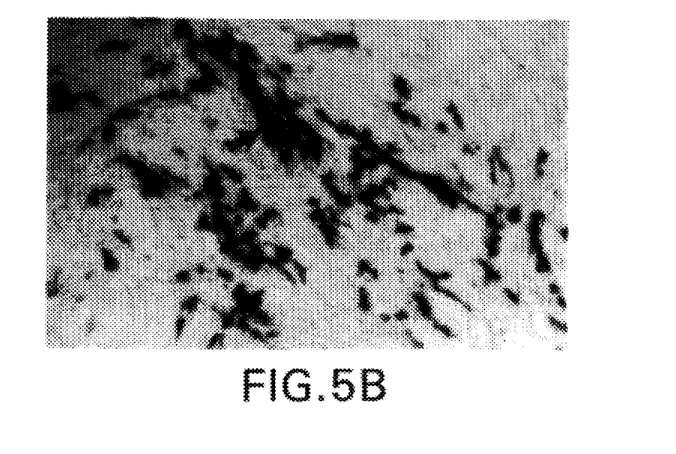
Figure 5C:
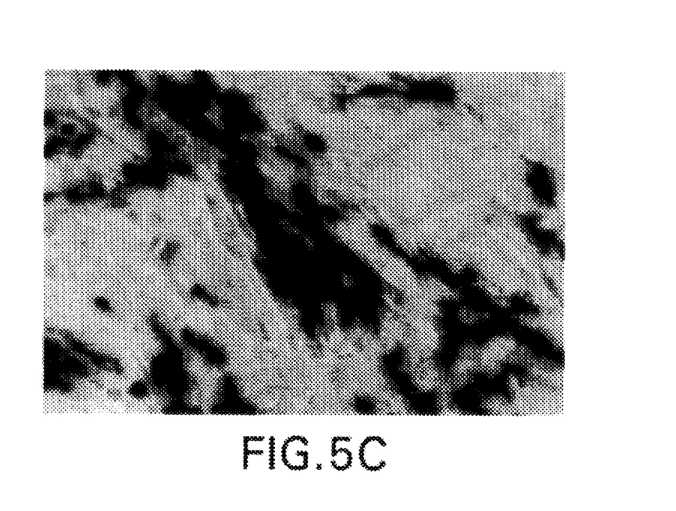

After 10 days the cultures were fixed and stained for alkaline phosphatase activity. Colonies of cells expressing high levels of alkaline phosphatase and closely resembling primordial germ cells of the mouse embryo were detected in many wells (see FIG. 5). Closely packed clusters of cells were present in some colonies (arrow in FIG. 5). In cultures of mouse embryo germ cells these colonies give rise to lines of pluripotential embryonic stem cells. Therefore, the identified human cells can give rise to cell lines.

Method for the isolation of embryonic stem cell lines form postnatal mammalian testis Testes are dissected and the tunica removed. The testes are then incubated at 32° C. with mild shaking in buffered saline containing bovine serum albumin and collagenase (final concentration approximately 0.5 mg/ml). When the tissue has dissociated the tubules are allowed to settle out and then washed in saline several times. The collagenase treatment is repeated to remove all the cells surrounding the tubules (Leydig cells and connective tissue). The tubules are then washed and treated with hyaluronidase in buffered saline (final concentration approximately 0.5 mg/ml) at 32° C. until the tubules are free of adherent material. The tubules are washed and placed onto tissue culture dishes coated with Poly-L-lysine. The Sertoli cells attach strongly to the dish and spread out, while the germ cells remain in suspension. The germ cells are collected and plated onto a layer of irradiated feeder cells comprising membrane bound and soluble stem cell factor, LIF and basic FGF as described above.

Generation of chimeras using non-murine ES cells

Chimeras utilizing non-murine non-human ES cells can likewise be produced utilizing the methods for murine described above and simply substituting the appropriate non-murine blastocyst for the species of ES utilized.

Throughout this application various publications are referenced. The disclosures of these publications in their entireties are hereby incorporated by reference into this application in order to more fully describe the state of the art to which this invention pertains.

The preceding examples are intended to illustrate but not limit the invention. While they are typical of those that might be used, other procedures known to those skilled in the art may be alternatively employed.

TABLE 1

Growth Factor Requirements for Secondary Cultures of PCG-Derived Cells

| Days in Culture | SF → SF + LIF + LIF + bFGF | SF + LIF + bFGF → S F + LIF + bFGF | SF + LIF + bFGF → S F |
|---|---|---|---|
| 1 | 112 ± 16 cells | 116 ± 20 cells | 142 ± 18 cells |
| 3 | 0.9 ± 0.6 colonies | 4.6 ± 1.1 colonies | 5.6 ± 0.8 colonies |
| 5 | 0.5 ± 0.4 colonies | 6.9 ± 1.2 colonies | 6.6 ± 1.3 colonies |

PGCs from 8.5 dpc embryos were cultured for 6 days on $SI^4$-m220 cells in the presence of either soluble rat SF alone or with soluble rat SF, LIF, an bFGF. Cultures were trypsinized and seeded into wells containing $SI^4$-m220 feeder cells with either soluble rat SF alone or soluble rat SF, LIF, and bFGF. Cultures were fixed and AP-positive cells (day 1) or colonies (days 2 and 5) counted. Numbers are mean ± SEM from four experiments. Secondary cultures show a reduced growth factor requirement compared with primary cultures.

REFERENCES

Bogler, O., Wren, D., Barnett, S. C., Land, H. and Noble, M. (1990). Cooperation between two growth factors promotes extended self-renewal and inhibits differentiation of oligodendrocyte-type-2 astrocyte (O-2A) progenitor cells. Proc. Natl. Acad. Sci. USA. 87, 6368–6372.

Dolci, S., Williams, D. E., Ernst, M. K., Resnick, J. L., Brannan, C. L., Lock, L. F., Lyman, S. D., Boswell, H. S. and Donovan, P. J. (1991). Requirement for mast cell growth factor for primordial germ cell survival in culture. Nature 352, 809–811.

Donovan, P. J., Stott, D., Cairns, L. A., Heasman, J. and Wylie, C. C. (1986). Migratory and postmigratory mouse primordial germ cells behave differenetly in culture. Cell 44, 831–838.

Ffrench-Constant, C., Hollingsworth, A., Heasman, J. and Wylie, C. C. (1991). Response to fibronectin of mouse primordial germ cells before, during and after migration. Development 113, 1365–1373.

Godin, I. and Wylie, C. C. (1991). TGFβ-1 inhibits proliferation and has a chemotropic effect on mouse primordial germ cells in culture. Development 113, 1451–1457.

Godin, I., Deed, R., Cooke, J., Zsebo, K., Dexter, M. and Wylie, C. C. (1991). Effects of the steel gene product on mouse primordial germ cells in culture. Nature 352, 807–809.

Ginsberg, M., Snow, M. H. L. and McLaren, A. (1990). Primordial germ cells in the mouse embryo during gastrulation. Development 110, 521–528.

Hogan, B. L. M., Costantini, F., and Lacy, E. (1986). Manipulating the Mouse Embryo: A Laboratory Manual. Cold Spring Harbor Publications, Cold Spring Harbor, N.Y.

Lawson, K. A. and Pederson, R. A. (1992). Clonal analysis of cell fate during gastrulation and early neurulation in the mouse in CIBA Foundation Symposium 165 Post Implantation Development in the Mouse John Wiley and Sons.

Mann, J. R., Gadi, I., Harbison, M. L., Abbondanzo, S. J. and Stewart, C. L. (1990). Androgenetic mouse embryonic stem cells are pluripotent and cause skeletal defects in chimeras: implications for genetic imprinting. Cell 62, 251–260.

Manova, K. and Bachvarova, R. F. (1991). Expression of c-kit encoded at the W locus of mice in developing embryonic germ cells and presumptive melanoblasts. Dev. Biol. 146, 312–324.

Matsui, Y., Toksok, D., Nishikawa, S., Nishikawa, S-I, Williams, D., Zsebo, K. and Hogan, B. L. M. (1991). Effect of steel factor and leukemia inhibitory factor on murine primordial germ cells in culture. Nature 353, 750–752.

Mintz, B. and Russell, E. S. (1957). Gene-induced embryological modifications of primordial germ cells in the mouse. J. Exp. Zoology 134, 207–230.

Noble, M., Murray, K., Stroobant, P., Waterfield, M. D. and Riddle, P. (1988). Platelet-derived growth factor promotes division and motility and inhibits premature differentiation of the oligodendrocyte/type-2 astrocyte progenitor cell. Nature 333, 560–562.

Noguchi, T. and Stevens, L. C. (1982). Primordial germ cell proliferation in fetal testes in mouse strains with high and low incidences of congenital testicular teratomas J. Natl. Cancer Inst. 69, 907–913.

Raff, M. C., Lillien, L. E., Richardson, W. D., Burne, J. F. and Noble, M. D. (1988). Platelet-derived growth factor from astrocytes drives the clock that times oligodendrocyte development in culture. Nature 333, 562–565.

Robertson, E. J. (1987). Embryo-derived stem cell lines in teratocarcinomas and embryonic stem cells: a practical approach. Ed. E. J. Robertson, IRL Press, Oxford pp. 71–112.

Robertson, E. J. (1987). Teratocarcinomas and embryonic stem cells: a practical approach, Ed. E. J. Robertson, IRL Press, Oxford.

Sedivy, J. M., and A. Joyner (1992). Gene Targeting, W. H. Freeman and Co.

Solter, D., Adams, N., Damjanov, I. and Koprowski, H. (1975). Control of teratocarcinogenesis in teratomas and differentiation, Eds. M. I. Sherman and D. Solter, Academic Press.

Solter, D. and Knowles, B. B. (1978). Monoclonal antibody defining a stage-specific mouse embryonic antigen (SSEA-1) Proc. Natl. Acad. Sci. USA 75, 5565–5569.

Soriano, P. and Jaenisch, R. (1986). Retroviruses as probes for mammalian development: allocation of cells to the somatic and germ cell lineages. Cell 46, 19–29.

Stevens, L. C. (1983). The origin and development of testicular, ovarian, and embryo-derived teratomas. Cold Spring Harbor Conferences on Cell Proliferation Vol. 10 Teratocarcinoma Stem Cells. Eds. Silver, L. M., Martin, G. R. and S. Strickland. 10, 23–36.

Stevens, L. C. and Makensen, J. A. (1961). Genetic and environmental influences on teratogenesis in mice. J. Natl. Cancer Inst. 27, 443–453.

Surani, M. A., Kothary, R., Allen, N. D., Singh, P. B., Fundele, R., Ferguson-Smith, A. C. and Barton, S. C. (1990). Genome imprinting and development in the mouse development. Suppl., 89–98.

Tam, P. P. L. and Snow, M. H. L. (1981). Proliferation and migration of primordial germ cells during compensatory growth in mouse embryos. J. Embryol. Exp. Morph. 64, 133–147.

Toksoz, D., Zsebo, K. M., Smith, K. A., Hu, S., Brankow, D., Suggs, S. V., Martin, F. H. and Williams, D. A. (1992). Support of human hematopoiesis in long-term bone marrow cultures by murine stromal cells selectively expressing the membrane-bound and secreted forms of the human homolog of the steel product, stem cell factor. Proc. Natl. Acad. Sci. USA, in press.

Yamaguchi, T. P., Conlon, R. A., and J. Rossant (1992). Expression of the fibroblast growth factor receptor FGFR-1/flg during gastrulation and segmentation in the mouse embryo. Development 152:75–88.

What is claimed is:

1. An isolated non-murine mammalian pluripotential cell wherein said cell exhibits the following characteristics:
   (a) can be maintained on feeder layers for at least 20 passages; and
   (b) gives rise to embryoid bodies and differentiated cells of multiple phenotypes in monolayer culture; and wherein said cell is derived from a primordial germ cell by the process of:
      (1) culturing a non-murine mammalian primordial germ cell in a composition comprising basic fibroblast growth factor, leukemia inhibitory factor, membrane associated steel factor, and soluble steel factor;
      (2) selecting cells that have characteristics (a) and (b), above, and
      (3) isolating said non-murine pluripotential cell.

2. The pluripotential cell of claim 1, having a mutation which renders a gone non-functional.

3. The pluripotential cell of claim 1, having an insertion of a functional gene.

4. A method of using a non-murine and non-human pluripotential cell of claim 1 to contribute to chimeras in vivo comprising:
   injecting the cell into a blastocyst of the same species of said cell;
   implanting the resultant chimeric blastocyst into a foster mother of the same species; and
   allowing the chimeric blastocyst to grow within the foster mother.

5. A method of using a non-murine and non-human pluripotential cell of claim 1 to contribute to chimeras in vivo comprising:
   aggregating the cell with a morula stage embryo of the same species of said cell;
   implanting the resultant chimeric embryo into a foster mother of the same species; and
   allowing the chimeric embryo to grow within the foster mother.

6. An isolated human pluripotential cell wherein said cell exhibits the following characteristics:
   (a) can be maintained on feeder layers for at least 20 passages; and
   (b) gives rise to embryoid bodies and differentiated cells of multiple phenotypes in monolayer culture; and wherein said cell is derived from a human primordial germ cell by the process of:
      (1) culturing a human primordial germ cell in a composition comprising basic fibroblast growth factor, leukemia inhibitory factor, membrane associated steel factor, and soluble steel factor;
      (2) selecting cells that have characteristics (a) and (b), above, and
      (3) isolating said human pluripotential cell.

7. A composition comprising:
   (A) a human pluripotential cell derived from a primordial germ cell wherein said cell exhibits the following characteristics:
      (1) can be maintained on feeder layers for at least 20 passages; and
      (2) gives rise to embryoid bodies and differentiated cells of multiple phenotypes in monolayer culture; and wherein said cell is derived from a primordial germ cell by the process of:
         (a) culturing a human primordial germ cell in a composition comprising basic fibroblast growth factor, leukemia inhibitory factor, membrane associated steel factor, and soluble steel factor;
         (b) selecting cells that have characteristics (a) and (b), above, and
         (c) isolating said human pluripotential cell; and
   (B) a fibroblast growth factor, leukemia inhibitory factor, membrane associated steel factor, and soluble steel factor, each in amounts sufficient to permit continued proliferation of said cell.

* * * * *